United States Patent [19]
Wuest et al.

[11] Patent Number: 5,126,371
[45] Date of Patent: Jun. 30, 1992

[54] DIARYLACETYLENES, THEIR PREPARATION AND THEIR USE

[75] Inventors: Hans-Heiner Wuest, Dossenheim; Fritz-Frieder Frickel, Deidesheim; Axel Nuerrenbach, Gruenstadt, all of Fed. Rep. of Germany

[73] Assignee: BASF Akteingesellschaft, Ludwigshafen, Fed. Rep. of Germany

[21] Appl. No.: 569,869

[22] Filed: Aug. 20, 1990

Related U.S. Application Data

[62] Division of Ser. No. 222,901, Jul. 22, 1988, Pat. No. 4,994,489, which is a division of Ser. No. 778,256, Sep. 20, 1985, Pat. No. 4,806,558.

[30] Foreign Application Priority Data

Sep. 22, 1984 [DE] Fed. Rep. of Germany ....... 3434946

[51] Int. Cl.$^5$ .................. A61K 31/045; A61K 31/085; A61K 31/11; A61K 31/12; A61K 31/135; A61K 31/165; A61K 31/275; C07C 255/50
[52] U.S. Cl. ..................................... 514/520; 514/546; 514/569; 514/617; 514/621; 514/622; 514/653; 514/655; 514/681; 514/700; 514/717; 514/718; 514/719; 514/730; 514/752; 558/414; 558/411; 558/423; 558/425; 560/255; 562/405; 562/462; 562/466; 562/467; 564/169; 564/172; 564/173; 564/180; 564/355; 564/360; 564/361; 564/362; 564/366; 564/384; 564/387
[58] Field of Search ............... 558/414, 411, 423, 425; 514/520, 859, 863, 546, 569, 617, 621, 622, 653, 655, 681, 700, 717, 718, 719, 730, 752; 570/128, 183; 568/377, 376, 440, 441, 632, 633, 634, 808; 564/169, 172, 173, 180, 355, 360, 361, 362, 366, 384, 387; 560/255; 562/405, 462, 466, 467

[56] References Cited

U.S. PATENT DOCUMENTS

| | | | |
|---|---|---|---|
| 4,186,264 | 1/1980 | Penrose et al. | 562/462 |
| 4,479,945 | 10/1984 | Szekely et al. | 562/462 |
| 4,760,174 | 7/1988 | Fickel et al. | 562/462 |
| 4,801,733 | 1/1989 | Wuest et al. | 562/462 |
| 4,806,558 | 2/1989 | Wuest et al. | 562/462 |

FOREIGN PATENT DOCUMENTS 3434948 9/1984 European Pat. Off. .

OTHER PUBLICATIONS

Wuest et al. Chem. Abstracts, vol. 105, No. 19; 172069g (1986).

*Primary Examiner*—Johann Richter
*Attorney, Agent, or Firm*—Keil & Weinkauf

[57] ABSTRACT

Novel diarylacetylenes of the formula I

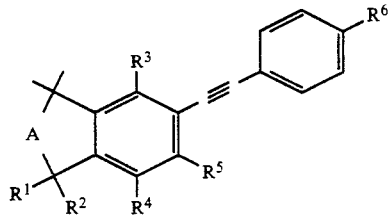

where A, $R^1$, $R^2$, $R^3$, $R^4$, $R^5$ and $R^6$ have the meanings stated in the description, are useful for the treatment of disorders.

6 Claims, No Drawings

DIARYLACETYLENES, THEIR PREPARATION AND THEIR USE

This application is a division of application Ser. No. 07/222,901, filed on Jul. 22, 1988, which is now U.S. Pat. No. 4,994,489, which was a divisional of Application Ser. No. 06/778,256, filed on Sep. 20, 1985, which is now U.S. Pat. No. 4,806,558.

The present invention relates to novel diarylacetylenes, processes for their preparation and their use in the treatment of disorders.

It is known that stilbene derivatives possess pharmacological actions in the topical and systemic therapy of neoplasias, acne, psoriasis and other dermatological affections. However, the action of these compounds is not always satisfactory.

We have found that diarylacetylenes of the formula I

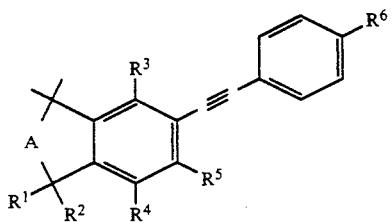

where $R^1$ and $R^2$ are each hydrogen or methyl, $R^3$ is hydrogen, methyl, hydroxyl or $C_1$-$C_6$-alkoxy, $R^4$ is hydrogen, methyl or methoxy, $R^5$ is hydrogen, halogen, methoxy or $C_1$-$C_4$-alkyl, A is a methylene or ethylene radical which is unsubstituted or substituted by $C_1$-$C_4$-alkyl or is —CH=CH—, —CHOH—$CH_2$— or —CO—$CH_2$—, and $R^6$ is hydrogen, methyl, nitrile, tetrazolyl, 2-oxazolinyl, $C_2$-$C_{10}$-ketal or a radical —$CHR^7$—$OR^8$, —$CHR^8$—$NR^9R^{10}$, —$COR^{11}$, —$CR^{12}$=CH—$COOR^{13}$ or —$CR^{12}$=CH—CO—$NR^{14}R^{15}$, where $R^7$ is hydrogen or $C_1$-$C_4$-alkyl, $R^8$ is hydrogen, $C_1$-$C_4$-alkyl, $C_1$-$C_{20}$-alkanoyl, unsubstituted or substituted benzoyl or a radical —P(O)(OR$^{13}$)$_2$ or —P(O) (NR$^{14}R^{15}$)$_2$ (where $R^{13}$ is hydrogen, unsubstituted or hydroxyl-substituted $C_1$-$C_8$-alkyl, unsubstituted or substituted aryl or aralkyl which is unsubstituted or substituted in the aryl moiety, and $R^{14}$ and $R^{15}$ are each hydrogen, unsubstituted or hydroxyl-substituted $C_1$-$C_6$-alkyl, or an unsubstituted or substituted aralkyl or aryl group, or $R^{14}$ and $R^{15}$, together with the nitrogen atom to which they are bonded, form a heterocyclic radical, $R^9$ and $R^{10}$ are each hydrogen, $C_1$-$C_4$-alkyl, $C_1$-$C_6$-alkanoyl or unsubstituted or substituted benzoyl or $R^9$ and $R^{10}$, together with the nitrogen atom to which they are bonded, form a heterocyclic radical, $R^{11}$ is hydrogen, halogen, $C_1$-$C_4$-alkyl or a radical —$NR^{14}R^{15}$ or —$OR^{13}$ (where $R^{13}$, $R^{14}$ and $R^{15}$ have the above meanings) and $R^{12}$ is hydrogen or methyl, and, where relevant, their physiologically tolerated salts possess a better action spectrum.

Preferred compounds of the formula I are those in which A is a methylene or ethylene radical substituted by methyl. Where $R^9$ and $R^{10}$, together with the nitrogen atom to which they are bonded, form a heterocyclic radical, the latter is preferably pyrrolidino, piperidino or morpholino. If $R^5$ and $R^{11}$ are each halogen, $R^5$ is preferably fluorine and $R^{11}$ is, in particular, chlorine or bromine. Preferred examples of substituents of the benzoyl group (cf. $R^8$, $R^9$ and $R^{10}$) are methoxy, nitro, methyl or halogen, in particular chlorine or bromine. Aryl ($R^{13}$, $R^{14}$ and $R^{15}$) is preferably phenyl which is unsubstituted or substituted by methyl, ethyl or nitro. Aralkyl ($R^{13}$, $R^{14}$ and $R^{15}$ is preferably benzyl which may be substituted in the aryl moiety in particular by methyl, methoxy or halogen. Examples of particularly suitable heterocyclic radicals —$NR^9R^{10}$ and —$NR^{14}R^{15}$ are pyrrolidino, piperidino and morpholino.

Typical examples of compounds according to the invention are:

4-[(5,6,7,8-Tetrahydro-5,5,8,8-tetramethylnaphth-2-yl)ethynyl]-benzoic acid,

4-[(5,6,7,8-tetrahydro-3,5,5,8,8-pentamethylnaphth-2-yl)ethynyl]-benzoic acid,

4-[(3-ethyl-5,6,7,8-tetrahydro-5,5,8,8-tetramethylnaphth-2-yl)-ethynyl]-benzoic acid, 4-[(3-fluoro-5,6,7,8-tetrahydro-5,5,8,8-tetramethylnaphth-2-yl)-ethynyl]-benzoic acid, 4-[(5,6,7,8-tetrahydro-3-methoxy-5,5,8,8-tetramethylnaphth-2-yl)ethynyl]-benzoic acid, 4-[(5,6,7,8-tetrahydro-1-hydroxy-5,5,3,8-tetramethylnaphth-2-yl)-ethynyl]-benzoic acid, 4-[(5,6,7,8-tetrahydro-1-methoxy-5,5,8,8-tetramethylnaphth-2-yl)-ethynyl]-benzoic acid, 4-[(5,6,7,8-tetrahydro-1,3-dimethoxy-5,5,8,8-tetramethylnaphth-2-yl)-ethynyl]-benzoic acid, 4-[(5,6,7,8-tetrahydro-1,4-dimethoxy-5,5,8,8-tetramethylnaphth-2-yl)-ethynyl]-benzoic acid, 4-[(5,6,7,8-tetrahydro-1-methoxy-4,5,5,8,8-pentamethylnaphth-2-yl)-ethynyl]-benzoic acid, 4-[(5,6,7,8-tetrahydro-1-methoxy-3,5,5,8,8-pentamethylnaphth-2-yl)-ethynyl]-benzoic acid, 4-[(5,6,7,8-tetrahydro-1,4-dimethoxy-3,5,5,8,8-pentamethylnaphth-2-yl)-ethynyl]-benzoic acid, 4-[(5,6,7,8-tetrahydro-5,5,8,8-tetramethyl-7-oxonaphth-2-yl)-ethynyl]-benzoic acid, 4-[(5,6,7,8-tetrahydro-7-hydroxy-5,5,8,8-tetramethylnaphth-2-yl)-ethynyl]-benzoic acid, 4-[(5,6,7,8-tetrahydro-3,8,8-trimethylnaphth-2-yl)-ethynyl]-benzoic acid, 4-[(2,3-dihydro-1,1,3,3-tetramethylinden-5(1H)-yl)-ethynyl]-benzoic acid, 4-[(2,3-dihydro-1,1,2,3,3-pentamethylinden-5(1H)-yl)-ethynyl]-benzoic acid, 4-[(2,3-dihydro-1,1,2,3,3,6-hexamethylinden-5(1H)-yl)-ethynyl]-benzoic acid, 4-[(5,6,7,8-tetrahydro-5,5,6,8,8-pentamethylnaphth-2-yl)-ethynyl]-benzoic acid, 4-[(5,6,7,8-dihydro-5,5,8,8-tetramethylnaphth-2-yl)-ethynyl]-benzoic acid, 4-[(1-hexyl-5,6,7,8-tetrahydro-3,5,5,8,8-pentamethylnaphth-2-yl)-ethynyl]-benzoic acid.

Other typical compounds are those which contain the following radicals instead of the carboxyl group: methoxycarbonyl-, ethoxycarbonyl-, propoxycarbonyl-, butoxycarbonyl-, benzyloxycarbonyl-, chlorocarbonyl-, cyano-, formyl-, hydroxymethyl-, methyl-, acetyl-, methoxymethyl-, ethoxymethyl-, benzyloxymethyl-, formyloxymethyl-, acetoxymethyl-, propionyloxymethyl-, hexadecanoyloxymethyl-, benzyloxymethyl-, 3,4-dimethoxybenzyloxymethyl-, dihydroxyphosphoryloxymethyl-, dimethoxyphosphoryloxymethyl-, bis(dimethylamido)phosphoryloxymethyl-, aminomethyl-, methylaminomethyl-, ethylaminomethyl-, propylaminomethyl-, butylaminomethyl-, acetylaminomethyl-, formylaminomethyl-, benzoylaminomethyl-, 4-methoxybenzoylaminomethyl-, dimethylaminomethyl-, morpholinomethyl-, pyrrolidinomethyl-, piperidinomethyl-, oxazolin-2-yl-, tetrazol-5-yl-, 1,3-dioxolan-2-yl-, dimethoxymethyl-, (E)-2-carbethoxyethenyl-, (E)-2-carboxyethenyl-, hydrogen, carbamyl-, methylcarbamyl-, dimethylcarbamyl-, morpholinocarbonyl- and phenylcarbamyl.

The compounds according to the invention can be prepared by a method in which a) where $R^6$ is cyano, a stilbene of the formula II

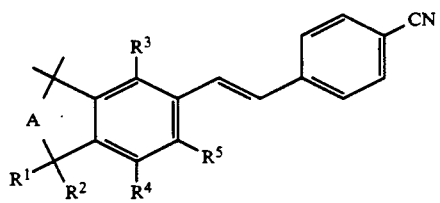

Where $R^1$, $R^2$, $R^3$, $R^4$, $R^5$ and A have the above meanings, is halogenated and 2 moles of hydrogen halide are then eliminated, or b) where $R^6$ is hydrogen, carboxyl, nitrile or formyl, an α-chlorobenzylphosphonate of the formula III

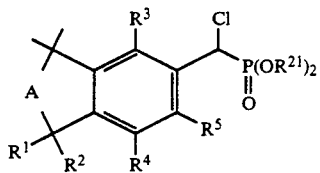

where $R^1$, $R^2$, $R^3$, $R^4$, $R^5$ and A have the above meanings, and $R^{21}$ is $C_1$–$C_3$-alkyl, is reacted with an aldehyde of the formula IV

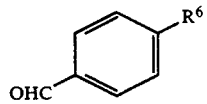

or c) where $R^6$ is methyl, nitrile or 1,3-dioxolan-2-yl, an α-chlorobenzylphosphonate of the formula V

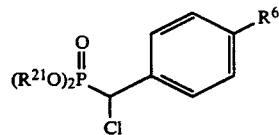

where $R^{21}$ has the above meanings, is reacted with an aldehyde of the formula VI

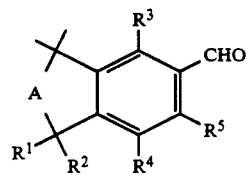

where $R^1$, $R^2$, $R^3$, $R^4$, $R^5$ and A have the above meanings, or d) where $R^6$ has the same meanings as stated under b), a monoarylacetylene of the formula VII

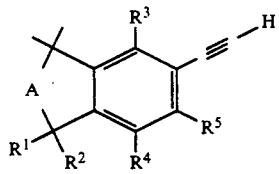

where $R^1$, $R^2$, $R^3$, $R^4$, $R^5$ and A have the above meanings, is reacted with an aryl halide of the formula VIII

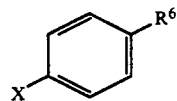

where X is halogen, in the presence of a catalyst and of a base, and, if desired, the resulting compound is converted to a further compound of the formula I by a standard method.

The halogenation of compounds of the formula II as described under a) is advantageously carried out using bromine, in a solvent at no higher than 50° C., preferably from −15° to 0° C. The solvent used is a chlorohydrocarbon, in particular chloroform or carbon tetrachloride. Instead of free bromine, it is also possible to use a complex of molecular bromine with a crown ether, e.g. dibenzo-18-crown-6, or a perbromide, e.g. tetrabutylammonium tribromide.

Suitable bases for eliminating two mole equivalents of hydrogen bromide from the resulting dibromo compound are the hydroxides, alcoholates, hydrides and amides of the alkali metals and alkaline earth metals. The reaction is advantageously carried out in a solvent; in aqueous solvents and/or when hydroxides are used as bases, the benzoic acids of the formula I (where $R^6$ is carboxyl) are formed by hydrolysis under the reaction conditions conventionally employed for the elimination reaction, i.e. at no higher than 200° C. The use of potassium hydroxide in n-butanol at 120° C. has proven particularly advantageous. Hydrolysis of the nitrile group is avoided if the reaction is carried out in the absence of hydroxyl ions, for example using potassium tert.-butylate as the base, in tetrahydrofuran or dimethyl sulfoxide, at from 25° to 60° C., or, particularly advantageously, in petroleum ether in the presence of a phase-transfer catalyst, preferably 18-crown-6, at the boiling point of the reaction mixture.

The compounds of the formula II are described in German Laid-Open Application DOS 3,202,125, or can be prepared by the processes stated therein.

The Wittig-Horner reactions described under b) and c) are carried out at no higher than 100° C., advantageously at from 20° to 50° C., under atmospheric pressure or in a closed vessel under superatmospheric pressure, if necessary with heating to the stated temperature.

These reactions can be carried out in the presence of a diluent or solvent, for example a lower saturated dialkyl ether, dialkylglycol ether or cyclic ether, such as diethyl ether, ethyl tert.-butyl ether, 1,2-dimethoxyethane, tetrahydrofuran or dioxane, an aromatic hydrocarbon, such as benzene or an alkylbenzene, e.g. toluene or xylene, a saturated aliphatic hydrocarbon, such as hexane, heptane or isooctane, a lower aliphatic ketone, such as acetone, methyl ethyl ketone or methyl isobutyl ketone, a dialkylformamide, such as dimethylformamide or diethylformamide, or a mixture of the stated solvents. Cyclic ethers, such as dioxane or tetrahydrofuran, and in particular dimethyl sulfoxide or mixtures of these are preferably used, the reaction taking place in general at no higher than 30° C.

The reactions are effected in the presence of a deprotonating agent, suitable compounds being alkali metal hydrides and alkali metal amides, in particular those of sodium and potassium, the sodium and potassium salts of dimethyl sulfoxide, alkyl-lithium compounds, such as n-butyl-lithium, or alkali metal alcoholates, preferably sodium methylate or potassium tert.-butylate.

The overall reaction [b) and c)] (Wittig-Horner reaction + elimination) surprisingly takes place particularly smoothly in a one-vessel process, using 2 mole equivalents of potassium tert.-butylate in dimethyl sulfoxide as the solvent (cf. J. Amer. Chem. Soc. 87 (1965), 2777).

In reaction d), the corresponding copper acetylides are prepared in situ from compounds of the formula VII in a conventional manner, these copper acetylides being reacted further with the aryl halides VIII, preferably the bromides or iodides, to give compounds of the formula I. Alternatively, the coupling reaction, starting directly from the acetylenes VII, can be catalyzed by triphenylphosphine complexes of palladium and nickel. In every case, it is advantageous if a base, e.g. an organic nitrogen base, such as triethylamine or pyridine, or an alkali metal alcoholate, such as sodium methylate or sodium phenolate, is present. If necessary, the reaction is carried out in a solvent, preferably dimethylformamide or tetrahydrofuran. The reaction takes place at from 50° to 150° C., advantageously 50° C. (aryl iodide) or 100° C. (aryl bromide).

The starting materials required for processes b, c and d are obtainable by known methods:

1-Aryl-1-chloromethylphosphonates of the formula III and of the formula V can be prepared by, for example, reacting the corresponding aromatic aldehyde with a dialkyl phosphite in the presence or absence of a catalytic amount of a base, e.g. triethylamine, sodium methylate or, particularly advantageously, potassium tert.-butylate, in a conventional manner; the 1-aryl-1-hydroxymethylphosphonates thus prepared are then usually treated with thionyl chloride or phosphorus oxytrichloride, this reaction being carried out in the presence of an acid acceptor, such as pyridine or triethylamine, where this is advantageous.

The aldehydes of the formula VI which are required for the Wittig-Horner reaction can be prepared by, for example, formylation of the corresponding tetralin or indane derivatives in the presence of a Lewis acid. The formylation is advantageously carried out using hexamethylene tetramin/trifluoroacetic acid. Tetrahydrotetramethylnaphthalene derivatives are described by T. F. Wood et al. in U.S. Pat. Nos. 3,442,640 and 3,499,751, or can be prepared from 2,5-dichloro-2,5-dimethylhexane and an appropriately substituted benzene by Friedel-Crafts alkylation by the method stated therein.

The monoarylacetylenes of the formula VII used as starting materials can be prepared, for example, as follows:

An aryl methyl ketone of the formula IX

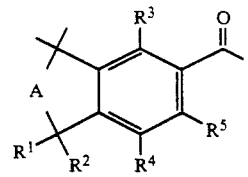

where A, $R^1$, $R^2$, $R^3$, $R^4$, $R^5$ have the stated meanings, is converted in a conventional manner with phosphorus pentachloride in the presence of a base, e.g. pyridine, at from 0° to 25° C. to the corresponding 1-aryl-1-chloroethylene, which is converted to a monoarylacetylene of the formula VII using a base, preferably potassium tert.-butylate, in an aprotic dipolar solvent, such as dimethyl sulfoxide, at from 25° to 40° C.

The substances prepared by the above methods a-d can then be converted further as follows:

The benzoates of the formula I (where $R^6$ is carboalkoxy) are, if desired, converted to the free carboxylic acid by hydrolysis of the esters. Conversely, the free acid can of course be esterified in a conventional manner.

The hydrolysis/esterification is advantageously carried out in the presence of a diluent, or solvent, for example a dialkylglycol ether or cyclic ether, such as 1,2-dimethoxyethane, tetrahydrofuran or dioxane, a lower aliphatic ketone, such as acetone, methyl ethyl ketone or methyl isobutyl ketone, or a lower aliphatic alcohol, such as methanol, ethanol, propanol or isopropanol, in the presence or absence of water or in a mixture of the stated solvents with water.

Preferred solvents are aqueous mixtures of ethanol and methanol, the reaction being carried out at the boiling point of the reaction mixture.

The hydrolysis is preferably effected in the presence of an alkali, such as an alkali metal hydroxide, carbonate or bicarbonate, in particular those of sodium or potassium, a tertiary organic base, such as pyridine or a lower trialkylamine, e.g. trimethylamine or triethylamine, as a mixture with water. The base is employed in a stoichiometric amount or in slight excess, based on the ester. Sodium hydroxide or potassium hydroxide is preferably used.

The esterification is advantageously carried out by first converting the carboxylic acid to one of its salts, and then treating this with an appropriate alkyl halide, preferably an alkyl bromide or iodide. Particularly suitable deprotonating agents for the preparation of the salts in situ are the carbonates, hydroxides and hydrides of the alkali metals. Advantageously, aprotic polar solvents, such as acetone, dimethylformamide, dimethyl sulfoxide and, in particular, methyl ethyl ketone, are used, the reaction being carried out at the boiling point of the reaction mixture.

The amides according to the invention can be prepared in a conventional manner by first converting the benzoic acids I (where $R^6$ is COOH) to derivatives possessing a more active carbonyl group, for example the acid halides, azides, imidazolides or anhydrides, the O-acyl-N,N'-dicyclohexylisoureas or p-nitrophenyl esters, and then treating these with an amine $HNR^{14}R^{15}$. In the case of particularly reactive amines, especially ammonia, direct amidolysis of esters (containing a radical $-OR^{13}$) is preferred.

A halide of a benzoic acid I (where $R^6$ is COOH), preferably the acyl chloride, can be converted to an oxazoline derivative of the formula (I) by reaction with 2-aminoethanol followed by cyclization.

A carboxylic acid, a carboxylate or a carboxamide of the formula I (where $R^6$ is $COR^{11}$) can be converted to the corresponding alcohol or amine in a conventional manner. Advantageously, the reduction is carried out using a metal hydride or alkali metal hydride in the presence of a suitable solvent. Preferably used metal hydrides are complex metal hydrides such as lithium aluminum hydride or diisobutyl aluminum hydride. When lithium aluminum hydride is employed, the solvent used is an ether, such as diethyl ether, dioxane or tetrahydrofuran, whereas when the reduction is carried out with diisobutyl aluminum hydride or an alkoxy sodium aluminum hydride, hydrocarbons such as hexane or toluene are preferably used.

The amines or alcohols thus obtained can be converted to the novel amides and esters of the formula (I) in a conventional manner with an alkanoyl halide or anhydride, an aralkyl halide or anhydride or an aroyl halide or anhydride, advantageously in an inert diluent or solvent, for example a lower aliphatic ketone, such as acetone, methyl ethyl ketone or methyl isobutyl ketone, a dialkylformamide, such as dimethylformamide or diethylformamide, or using excess acylating agent as the diluent or solvent. The reactions are preferably effected in the presence of a base as an acid acceptor, at from $-20°$ C. to the boiling point of the reaction mixture. Suitable bases are alkali metal carbonates, bicarbonates, hydroxides and alcoholates, in particular those of sodium and potassium, basic oxides, such as aluminum oxide or calcium oxide, tertiary organic bases, such as pyridine and lower trialkylamines, e.g. trimethylamine or triethylamine. The bases can be used in a catalytic amount or in a stoichiometric amount or in slight excess, based on the alkylating agent employed.

Similarly, an alcohol I (where $R^6$ is $CHR^7$—OH) can be converted to the corresponding phosphate or phosphoramide with a phosphoryl halide, preferably a phosphoryl chloride $CL$—$P(O)$ $(OR^{13})_2$ or $CL$—$P(O)$ $(NR^{14}R^{15})_2$, or a phosphoric anhydride. For the preparation of dihydrogen phosphates (where $R^{13}$ is H), the trichlorimidate of phosphoric acid proved a particularly advantageous phosphorylation reagent.

An alcohol of the formula I can be converted to the corresponding ether with an alkylhalide $R^{15}$—I, $R^{15}$—Br or $R^{15}$—Cl in the presence of an alkali metal hydride, preferably sodium hydride, or of an alkyllithium compound, preferably n-butyl-lithium, in an organic solvent, such as tetrahydrofuran, dioxane, 1,2-dimethoxyethane, methyl tert.-butyl ether or, where sodium hydride is used, dimethylformamide, at from $-10°$ to $40°$ C.

An alcohol of the formula I can be oxidized to the corresponding aldehyde with a suitable oxidizing agent, preferably manganese (IV) oxide, if appropriate on an inorganic carrier, such as silica gel or alumina. The reaction is advantageously carried out in an inert organic solvent, for example a hydrocarbon, such as hexane, or an ether, e.g. tetrahydrofuran, or a mixture of the stated solvents and diluents, at from $-10°$ to $30°$ C. The reaction time required depends essentially on the oxidation activity of the manganese (IV) oxide employed.

An aldehyde I (where $R^6$ is —CHO) can also be obtained by reduction of the corresponding nitrile with diisobutyl aluminum hydride in a solvent, preferably in toluene, hexane, tetrahydrofuran or a mixture of these, at from $-40°$ C. to room temperature.

The aldehydes and ketones of the formula I are furthermore obtained by hydrolyzing their ketals, usually in the presence of an acid as catalyst, preferably dilute hydrochloric or sulfuric acid, at from $20°$ C. to the boiling point of the reaction mixture. Advantageously, the reaction is carried out in a water-miscible solvent, such as acetone, dioxane, tetrahydrofuran or, preferably, a short-chain alcohol, such as methanol or ethanol.

A carbonyl compound of the formula I (where $R^6$ is —$COR^{12}$) can be subjected to a Wittig-Horner reaction with a phosphorus compound of the formula (X) or (XI)

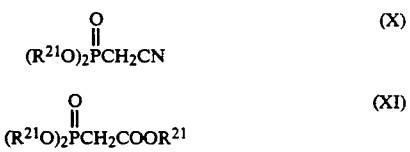

where $R^{21}$ has the stated meanings, the reaction advantageously being carried out in a solvent, preferably tetrahydrofuran, dimethylformamide or dimethyl sulfoxide, in the presence of a base conventionally employed for such olefinations, e.g. sodium hydride or sodium methylate. The reaction takes place at up to $100°$ C., advantageously at from $20°$ to $50°$ C.

The nitrile or ester group is, if desired, then converted to other functional groups by the methods described above and below.

A nitrile of the formula I (where $R^6$ is —CN) can be hydrolyzed in a conventional manner with acid catalysis or, advantageously, base catalysis to give the corresponding carboxylic acid. Preferably used bases are alkali metal hydroxides, in particular potassium hydroxide which is used in excess. The solvent used is, as a rule, a water-miscible alcohol, e.g. methanol, ethanol, isopropanol or n-butanol. The reaction is usually carried out at the boiling point of the reaction mixture.

The corresponding tetrazoles can be obtained from the nitriles I (where $R^6$ is —CN) by means of an addition reaction with an azide, for example an alkali metal azide, preferably sodium azide, in the presence of aluminum chloride or ammonium chloride. Preferably used solvents are cyclic ethers, such as dioxane or tetrahydrofuran, and in particular dimethylformamide or mixtures of these, the reaction taking place in general at from $60°$ to $100°$ C.

Some of the novel compounds possess an acidic hydrogen atom and can therefore be converted with a base in a conventional manner to a physiologically tolerated, readily water-soluble salt. Examples of suitable salts are ammonium salts, alkali metal salts, in particular those of sodium, potassium and lithium, alkaline earth metal salts, in particular those of calcium and magnesium, and salts with suitable organic bases, such as lower alkylamines, e.g. methylamine, ethylamine or cyclohexylamine, or with substituted lower alkylamines, in particular hydroxyl-substituted alkylamines, such as diethanolamine, triethanolamine or tris-(hydroxymethyl)-aminomethane, and with piperidine and morpholine.

If required, the resulting novel amines of the formula (I) are converted to addition salts with physiologically tolerated acids by a conventional procedure. Examples of suitable conventional physiologically tolerated inorganic acids are hydrochloric acid, hydrobromic acid, phosphoric acid and sulfuric acid, and examples of organic acids are oxalic acid, maleic acid, fumaric acid, lactic acid, tartaric acid, malic acid, citric acid, salicylic acid, adipic acid and benzoic acid. Other suitable acids are described in Fortschritte der Arzneimittelforschung, volume 10, pages 224-225, Birkhäuser Verlag, Basel and Stuttgart 1966.

Because of their pharmacological properties, the novel compounds and their physiologically tolerated salts can be used in the topical and systemic therapy and prophylaxis of precanceroses and carcinomas of the skin, the mucous membranes and internal organs, in the topical and systemic therapy of acne, psoriasis and other dermatological disorders accompanied by pathologically changed cornification, and for the treatment of rheumatic disorders, in particular those of an inflammatory or degenerative nature which affect the joints, muscles, tendons and other parts of the locomotor system. A preferred area of indication in addition to the therapy of dermatological disorders is the prophylatic and therapeutic treatment of precanceroses and tumors.

The pharmacological actions can be demostrated, for example, in the following test models. In in vitro hamster tracheal tissue, the novel compounds eliminate the keratinization which sets in after vitamin A deficiency. This keratinization forms part of the early phase of carcinogenesis, which is inhibited in vivo by the novel compounds of the formula (I) using a similar technique after being induced by chemical compounds or high-energy radiation or after viral cell transformation. This method is described in Cancer Res. 36 (1976), 964-972, Nature 250 (1974), 64-66 and Nature 253 (1975), 47-50.

The compounds according to the invention also inhibit the proliferation rates of certain cells showing malignant changes. This method is described in J. Natl. Cancer Inst. 60 (1978), 1035-1041, Experimental Cell Research 117 (1978), 15-22 and Proc. Natl. Acad. Sci. USA 77 (1980), 2937-2940.

The antiarthritic action of the novel compounds can be determined in a conventional manner in animal experiments using the adjuvant arthritis model. The dermatological activity, for example in the treatment of acne, can be demonstrated by, inter alia, determining the comedolytic activity and the ability to reduce the number of cysts in the rhino mouse model.

This method is described by L. H. Kligman et al. in The Journal of Investigative Dermatology 73 (1978), 354-358, and J. A. Mezick et al. in Models of Dermatology (Ed. Maibach, Lowe), vol. 2, pages 59-63, Karger, Basel (1985).

The test substance in a suitable carrier was applied topically (100 μl) to the entire back area of the Rhino mouse, application being effected once a day on five successive days per week for two weeks. About 72 hours after the final treatment, the dorsal skin was removed, and left in 0.5% strength acetic acid for 18 hours at 4°-6° C. Thereafter, an area of about 2×5 cm² was cut out and the epidermis was peeled off, placed on a microscope slide (with the dermal side upward) and washed water-free with alcohol/xylene until the epidermis appeared transparent. The sample was fixed by coating it with Permount, and evaluated microscopically. The diameters of 10 utricles in 5 freely selected areas were measured in each case, and the mean reduction in the utricle diameter was calculated from this by comparison with the untreated control group. The Table below shows the results obtained.

TABLE

| Substance | Dose mg/ml | Reduction in the utricle diameter in % |
|---|---|---|
| 6 | 0.01 | 81.9 |
|  | 0.001 | 70.9 |
|  | 0.0001 | 51.3 |
| 14 | 0.02 | 66.9 |
| 12 | 2 | 78.0 |
|  | 0.2 | 38.2 |
| 1 | 2 | 54.7 |

Accordingly, the present invention furthermore relates to therapeutic agents for topical and systemic administration which contain a compound of the formula (I) as an active compound, in addition to conventional carriers or diluents, and to the use of a compound of the formula (I) for the preparation of a drug.

The therapeutic agents or formulations are prepared in a conventional manner, for example by using an appropriate dose of the active compound with conventional solid or liquid carriers or diluents and conventional pharmaceutical auxiliaries, in accordance with the desired route of administration.

Accordingly, the agents can be administered perorally, parenterally or topically. Examples of formulations of this type are tablets, film tablets, coated tablets, capsules, pills, powders, solutions or suspensions, infusion or injectable solutions, and pastes, ointments, gels, creams, lotions, dusting powders, solutions or emulsions and sprays.

The therapeutic agents can contain the compounds used according to the invention in a concentration of from 0.000001 to 1%, preferably from 0.00001 to 0.1%, for local administration, and preferably in a single dose of from 0.1 to 50 mg for systemic administration, and can be administered daily in one or more doses, depending on the nature and severity of the illness.

Examples of conventional pharmaceutical auxiliaries are alcohols, such as isopropanol, oxyethylated castor oil or oxyethylated hydrogenated castor oil, polyacrylic acid, glycerol monostearate, liquid paraffin, vaseline, wool fat, polyethylene glycol 400, polyethylene glycol 400 stearate and oxyethylated fatty alcohols for local administration, and lactose, propylene glycol, ethanol, starch, talc and polyvinylpyrrolidone for systemic administration. If required, an antioxidant, for example tocopherol, butylated hydroxyanisole or butylated hydroxytoluene, or flavor-improving additives, stabilizers, emulsifiers, lubricants, etc., may be added to the preparations. All substances used in the preparation of pharmaceutical formulations must be toxicologically acceptable and compatible with the active compounds used.

A.

SYNTHESIS OF STARTING MATERIALS

General method for the preparation of diethyl 1-chloro-1-arylmethylphosphonates 7.5 g (0.067 mole) of potassium tert.-butylate were added all at once to 152 g (1.1 moles) of diethyl phosphite and 1 mole of the corresponding aromatic aldehyde. The subsequent increase in temperature was controlled via the stirring speed so that the temperature did not exceed 70°-90° C. In some cases, external cooling for a short time is required. When the mixture had cooled, it was stirred with water and ethyl acetate, the organic phase was separated off, dried over sodium sulfate and evaporated down, and the residue was finally recrystallized from petroleum ether or ether to give the pure diethyl 1-hydroxy-1-arylmethylphosphonate. This was introduced a little at a time into the stated amount of thionyl chloride, the temperature increasing to about 35° C. Stirring was continued for 30 minutes, and excess thionyl chloride was distilled off under reduced pressure, residual thionyl chloride being removed by adding toluene and carrying out distillation again. The resulting crude diethyl 1-chloro-1-arylmethylphosphonate was purified by the method stated in each case.

a) Diethyl 1-chloro-1-(4-tolyl)methylphosphonate 115.4 g (0.96 mole) of 4-tolylaldehyde were converted to 177.8 g (72%) of diethyl 1-hydroxy-1-(4-tolyl)methylphosphonate [cf. Abramov, Zh. obshch. Chim. 27 (1957), 169, 172, and CA 61 (1957), 12878], and 73 g (66%) of the title compound of boiling point 139° C./0.3 mbar were obtained from 98 g (0.38 mole) of the last-mentioned compound and 188 ml of thionyl chloride after distillation.

b) Diethyl 1-chloro-1-(5,6,7,8-tetrahydro-5,5,8,8-tetramethylnaphth-2-yl)-methylphosphonate 216 g (1 mole) of 2-formyl-5,6,7,8-tetrahydro-5,5,8,8-tetramethylnaphthalene were converted to 251 g (71%) of diethyl 1-hydroxy-1-(5,6,7,8-tetrahydro-5,5,8,8-tetramethylnaphth-2-yl)-methylphosphonate of melting point 93°-95° C., and 188.4 g (88%) of the title compound were obtained from 203 g (0.57 mole) of the last-mentioned compound and 287 ml of thionyl chloride. Since the material decomposes during distillation, the working up procedure was modified as follows. The crude product obtained after removal of the thionyl chloride was dissolved in toluene, and the solution stirred with 5 g of potassium carbonate for 20 minutes. The solid was filtered off, the solvent was removed and the solidified mass was comminuted in a mortar. The material thus obtained (m.p. 65°-66° C.) was about 85% pure according to the H-NMR spectrum.

General method for the preparation of monoarylacetylenes

A solution of 0.38 mole of the corresponding acetophenone derivative in 260 ml of pyridine was added dropwise to a mixture of 260 g of phosphorus pentachloride, 350 ml of pyridine and 2.6 l of toluene, the mixture having been heated to 40° C. beforehand. The mixture was then stirred for 3 hours under reflux and for 16 hours at room temperature, after which the toluene phase was decanted, washed with water (exothermic), dried with $Na_2SO_4$ and evaporated down. The residue was dissolved in 51 ml of dimethyl sulfoxide, and 28.6 g of potassium tert.-butylate in 120 ml dimethyl sulfoxide were added dropwise to this solution at 20°-35° C. Stirring was continued for a further 16 hours at room temperature, after which the mixture was poured onto water and extracted three times with ether, and the combined ether phases were washed with water, dried over $Na_2SO_4$ and evaporated down. The crude acetylene was purified by distillation.

The following compounds were prepared by this method:

(5,6,7,8-Tetrahydro-5,5,8,8-tetramethylnaphth-2-yl)-ethyne, b.p. 82°-94° C. (0.1 mbar), yield 9%, from 2-acetyl-5,6,7,8-tetrahydro-5,5,8,8-tetramethylnaphthalene.

(1,2-Dihydro-1,1,2,3,3-pentamethyl-5(1H)-indenyl)-ethyne, b.p. 85°-90° C. (0.3 mbar), yield 27%, from 5-acetyl-1,2-dihydro-1,1,2,3,3-pentamethyl-(1H)-indene.

(1,2-Dihydro-1,1,3,3-tetramethyl-5(1H)-indenyl)-ethyne, b.p. 94° C. (2 mbar), yield 9%, from 5-acetyl-1,2-dihydro-1,1,3,3-tetramethyl-(1H)-indene.

(5,6,7,8-Tetrahydro-3,8,8-trimethylnaphth-2-yl)-ethyne, b.p. 100°-105° C. (1 mbar), yield 12%, from 2-acetyl-5,6,7,8-tetrahydro-3,8,8-trimethylnaphthalene.

B.

SYNTHESIS OF THE COMPOUNDS ACCORDING TO THE INVENTION

EXAMPLE 1

4-[(5,6,7,8-tetrahydro-5,5,8,8-tetramethylnaphth-2-yl)-ethynyl]-benzonitrile a) 6.7 g (0.014 mole) of 1,2-dibromo-1-(4-cyanophenyl)-2-(5,6,7,8-tetrahydro-5,5,8,8-tetramethyl-naphth-2-yl)-ethane (cf. Example 6a) were suspended in 26 ml of petroleum ether. After the addition of 3.2 g (0.028 mole) of potassium tert.-butylate, the temperature of the reaction mixture increased to 50° C. The mixture was refluxed for 1 hour, 20 mg (0.1 mole) of 18-crown-6 were added, and refluxing was continued for a further 10 hours. Thereafter, the mixture was poured onto 500 ml of ice water and extracted twice with petroleum ether, and the organic phase was washed with water, dried over sodium sulfate and evaporated down under reduced pressure to give 4.3 g of crude product. Recrystallization from ethanol gave 1.9 g (43%) of the title compound of melting point 166° C.

b) A solution of 13.8 g (0.123 mole) of potassium tert.-butylate in 65 ml of dimethyl sulfoxide was added dropwise in the course of 30 minutes to a solution of 22.6 g (0.06 mole) of diethyl 1-chloro-1-(5,6,7,8-tetrahydro-5,5,8,8-tetramethylnaphth-2-yl)-methylphosphonate (about 85% strength) and 7.86 g (0.06 mole) of 4-cyanobenzaldehyde in 190 ml of dry dimethyl sulfoxide at room temperature. Stirring was continued for 1 hour, after which the mixture was poured onto 1 liter of ice water and acidified with a little dilute hydrochloric acid, and the resulting crystals were filtered off under suction. Recrystallization from ethanol gave 9.2 g (49%) of the title compound of melting point 157° C.

c) A mixture of 4 g (19 millimoles) of (5,6,7,8-tetrahydro-5,5,8,8-tetramethylnaphth-2-yl)-ethyne, 2.8 g (12.5 millimoles) of 4-bromobenzonitrile, 50 mg of palladium (II) acetate, 100 mg of triphenylphosphine and 25 ml of degased anhydrous triethylamine was refluxed for 4 hours under nitrogen. Thereafter, solid material was filtered off and the filtrate was evaporated down.

Recrystallization of the residue gave 2.6 g (66%) of the title compound, which was hydrolyzed to the carboxylic acid without further purification (cf. Example 6c).

EXAMPLE 2

4-[(1,2-Dihydro-1,1,2,3,3-pentamethyl-5(1H)-indenyl)-ethynyl]-benzonitrile

Using a process similar to that described in Example 1c, 4 g (19 millimoles) of (1,2-dihydro-1,1,2,3,3-pentamethyl-5(1H)-indenyl)-ethyne and 2.8 g (12.5 millimoles) of 4-bromobenzonitrile were converted to the title compound. 2 g (51%) of product of melting point 110°-112° C. were obtained after recrystallization from isopropanol, the residue from the filtrate being extracted with sodium bicarbonate solution/methylene chloride and further treated in a conventional manner.

EXAMPLE 3

4-[(1,2-Dihydro-1,1,3,3-tetramethyl-5(1H)-indenyl)-ethynyl]-benzonitrile

Using a process similar to that described in Example 1c, 3.7 g (19 millimoles) of (1,2-dihydro-1,1,3,3-tetramethyl-5(1H)-indenyl)-ethyne and 2.8 g (12.5 millimoles) of 4-bromobenzonitrile were converted to the title compound. 1.4 g (37%) of product were obtained after recrystallization from ethanol, and were hydrolyzed to the carboxylic acid without further purification (cf. Example 6c).

EXAMPLE 4

4-[(5,6,7,8-Tetrahydro-3,8,8-trimethylnaphth-2-yl)-ethynyl]-benzonitrile

Using a process similar to that described in Example 1c, 4.4 g (22 millimoles) of (5,6,7,8-tetrahydro-3,8,8-trimethylnaphth-2-yl)-ethyne and 2.7 g (15 millimoles) of 4-bromobenzonitrile were converted to the title compound. 1.3 g (29%) of product of melting point 128°–130° C. were obtained after recrystallization from ethanol.

EXAMPLE 5

4-[(5,6,7,8-Tetrahydro-3-methoxy-5,5,8,8-tetramethylnaphth-2-yl)-ethynyl]-benzonitrile Using a process similar to that described in Example 1a, 34 g (0.1 mole) of 4-[2-(5,6,7,8-tetrahydro-3-methoxy-5,5,8,8-tetramethylnaphth-2-yl)-1-ethenyl]-benzonitrile were converted to 6.9 g (20%) of crude product, from which 2.6 g of the title compound of melting point 165°–167° C. were obtained by recrystallization.

EXAMPLE 6

4-[(5,6,7,8-Tetrahydro-5,5,8,8-tetramethylnaphth-2-yl)-ethynyl]-benzoic acid a) A solution of 148 g (0.09 mole, 4.7 ml) of bromine in 25 ml of chloroform was added dropwise to a suspension of 26.5 g (0.08 mole) of (E)-4-[2-(5,6,7,8-tetrahydro-5,5,8,8-tetramethylnaphth-2-yl)-1-ethynyl]-benzonitrile in 120 ml of chloroform at from −15° to 10° C. The reaction mixture was stirred for a further 15 minutes and evaporated down in a rotary evaporator, and the residue was recrystallized from methanol. 26.7 g (70%) of 1,2-dibromo-1-(4-cyanophenyl)-2-(5,6,7,8-tetrahydro-5,5,8,8-tetramethylnaphth-2-yl)-ethane were obtained as a mixture of diastereomers of melting point 174°–175° C.

50.7 g (0.11 mole) of these compounds were added to an alkaline solution of 60.2 g of potassium hydroxide in 143 ml of n-butanol, and the mixture was refluxed for 1 hour. The cooled reaction mixture was poured onto 1.5 liters of ice water and acidified with concentrated hydrochloric acid. The precipitate which separated out was filtered off under suction, washed with water and then with methanol, dried in a stream of nitrogen and recrystallized from isopropanol to give 26.9 g (74%) of the title compound of melting point 265°–266° C.

b) 22.6 g (0.06 mole) of diethyl 1-chloro-1-(5,6,7,8-tetrahydro-5,5,8,8-tetramethylnaphth-2-yl)-methylphosphonate (about 85% strength) and 9 g of 4-carboxybenzaldehyde in 190 ml of dry dimethyl sulfoxide were initially taken. 21 g (0.185 mole) of potassium tert.-butylate in 65 ml of dimethyl sulfoxide were added dropwise to the stirred mixture at room temperature. Stirring was continued for 1 hour, after which the reaction mixture was poured onto 1 liter of ice water and acidified with 20% strength sulfuric acid. The resulting precipitate was filtered off under suction, washed with water and recrystallized from isopropanol to give 14 g (70%) of the title compound. Carrying out recrystallization twice more gave 6 g of pure material of melting point 263°–264° C.

c) 2.6 g (8 millimoles) of 4-[(5,6,7,8-tetrahydro-5,5,8,8-tetramethylnaphth-2-yl)-ethynyl]-benzonitrile (Example 1) and 4.6 g of 85% strength potassium hydroxide in 17 ml of n-butanol were refluxed for 1.5 hours. The cooled reaction mixture was dissolved in 100 ml of water and the solution was extracted three times with ether. The aqueous phase was freed from residual ether under reduced pressure and acidified with 2N HCL. The precipitate which had separated out was filtered off under suction, washed with water and dried in a stream of nitrogen. 2.1 g of crude product remained. Recrystallization from isopropanol gave 1.2 g (44%) of the title compound of melting point 252°–256° C., which had a purity of 99.9% according to HPLC (C18 reversed phase; 9:1 acetonitrile/H2O+0.1% of acetic acid; 100 ml/min; $t_R$: 7 min).

EXAMPLE 7

4-[(5,6,7,8-Tetrahydro-3-methoxy-5,5,8,8-tetramethylnaphth-2-yl)-ethynyl]-benzoic acid Using a process similar to that described in Example 6c, 1 g (2 millimoles) of 4-[(5,6,7,8-tetramethyl-3-methoxy-5,5,8,8-tetramethylnaphth-2-yl)-ethynyl]-benzonitrile (Example 5) was converted to 0.5 g (64%) of the title compound of melting point 231°–234° C., extraction with ether being omitted and the crude crystals being recrystallized from methanol.

EXAMPLE 8

4-[(1,2-Dihydro-1,1,2,3,3-pentamethyl-5(1H)-indenyl)-ethynyl]-benzoic acid

Using a process similar to that described in Example 6c, 2 g (6 millimoles) of 4-[(-1,2-dihydro-1,1,2,3,3-pentamethyl-5(1H)-indenyl)-ethynyl]-benzonitrile (Example 2) were converted to 1.1 g (55%) of the title compound of melting point 267°–270° C., the extraction with ether and the recrystallization being omitted.

EXAMPLE 9

4-[(1,2-Dihydro-1,1,3,3-tetramethyl-5(1H)-indenyl)-ethnyl]-benzoic acid

Using a process similar to that described in Example 6c, 1.4 g (5 millimoles) of 4-[(1,2-dihydro-1,1,3,3-tetramethyl-5(1H)-indenyl)-ethynyl]-benzonitrile (Example 3) were converted to 0.9 g (60%) of the title compound of melting point 236° C., the extraction with ether being omitted and the crude crystals being recrystallized from isopropanol.

EXAMPLE 10

4-[(5,6,7,8-Tetrahydro-3,8,8-trimethylnaphth-2-yl)-ethynyl]-benzoic acid 1 g (3.3 millimoles) of 4-[(5,6,7,8-tetrahydro-3,8,8-trimethylnaphth-2-yl)-ethynyl]-benzonitrile (Example 4) in 19 ml of ethanol and 19 ml of 10N NaOH were refluxed for 6.5 hours. The mixture was cooled, poured onto water and acidified with 2N HCL, and the precipitated crystals were filtered off under suction, washed with water and dried to give 1 g (95%) of the title compound of melting point 203°–206° C.

EXAMPLE 11

Ethyl 4-[(5,6,7,8-tetrahydro-5,5,8,8-tetramethylnaphth-2-yl)-ethynyl]-benzoate 3.0 g (9 millimoles) of 4-[(5,6,7,8-tetrahydro-5,5,8,8-tetramethylnaphth-2-yl)-ethynyl]-benzoic acid, 4 g (30 millimoles) of potassium carbonate and 2.9 g (18.9 millimoles) of iodoethane in 27 ml of butan-2-one were refluxed until conversion was complete (monitored by thin layer chromatography). When the mixture had cooled, the solid was filtered off, the filtrate was evaporated down and the residue was recrystallized from methanol to give 2.1 g (65%) of the title compound of melting point 137°–138° C.

EXAMPLE 12

2-(5,6,7,8-Tetrahydro-5,5,8,8-tetramethylnaphth-2-yl)-1-[4-(1H-tetrazol-5-yl)-phenyl]-acetylene 2.15 g (0.033 mole) of sodium azide, 1.77 g (0.033 mole) of ammonium chloride and 9.2 g (0.03 mole) of 4-[(5,6,7,8-tetrahydro-5,5,8,8-tetramethylnaphth-2-yl)-ethynyl]-benzonitrile in 30 ml of absolute dimethylformamide were stirred for 12 hours at 120° C. The cooled reaction mixture was then poured onto 0.5 liter of water and acidified with a little hydrochloric acid. The crystals which had separated out were filtered off under suction, washed on the filter several times with water and then with methanol, sucked dry while hot, and dried in a stream of nitrogen. 9.0 g (84%) of the title compound of melting point 227°–228° C. were obtained.

EXAMPLE 13

(5,6,7,8-Tetrahydro-3-methoxy-5,5,8,8-tetramethyl-naphth-2-yl)-(4-tolyl)-acetylene A solution of 20.2 g (0.18 mole) of potassium tert.-butylate in 45 ml of dimethyl sulfoxide was added dropwise to a solution of 23.2 g (0.09 mole) of diethyl 1-chloro-1-(4-tolyl)-methylphosphonate and 22.1 g (0.09 mole) of 2-formyl-5,6,7,8-tetrahydro-3-methoxy-5,5,8,8-tetramethylnaphthalene in 270 ml of dry dimethyl sulfoxide at room temperature. The mixture was stirred for 30 minutes, poured onto 1 liter of ice water and extracted three times with ether. The ether phase was washed twice with water, dried over sodium sulfate and evaporated down to give 22.6 g (76%) of a slightly impure product. Recrystallization from methanol gave 15.2 g (51%) of the pure title compound of melting point 127° C.

EXAMPLE 14

(5,6,7,8-Tetrahydro-5,5,8,8-tetramethylnaphth-2-yl)-(4-tolyl)-acetylene

Using a process similar to that described in Example 13, 61.4 g (0.22 mole) of diethyl 1-chloro-1-(4-tolyl)-methylphosphonate, 51.1 g (0.22 mole) of 2-formyl-5,6,7,8-tetrahydro-5,5,8,8-tetramethylnapthalene and 50 g (0.44 mole) of potassium tert.-butylate were reacted for 1 hour to give 37.1 g (56%) of the title compound of melting point 99° C., the reaction mixture being poured onto water and acidified, and the precipitated solid being filtered off under suction and recrystallized twice from methanol.

EXAMPLE 15

(3-Fluoro-5,6,7,8-tetrahydro-5,5,8,8-tetramethylnaphth-2-yl)-(4-tolyl)-acetylene Using a process similar to that described in Example 13, 27.7 g (0.1 mole) of diethyl 1-chloro-1-(4-tolyl)-methylphosphonate, 23.4 g (0.1 mole) of 3-fluoro-2-formyl-5,6,7,8-tetrahydro-5,5,8,8-tetramethylnaphthalene and 22.5 g (0.2 mole) of potassium tert.-butylate were reacted for 1 hour to give the title compound. Recrystallization from isopropanol gave 16.4 g (51%) of product of melting point 60°–61° C.

EXAMPLE 16

(3-Ethyl-5,6,7,8-tetrahydro-5,5,8,8-tetramethylnaphth-2-yl)-(4-tolyl)-acetylene

Using a process similar to that described in Example 13, 27.7 g (0.1 mole) of diethyl 1-chloro-1-(4-tolyl)-methylphosphonate, 24.4 g (0.1 mole) of 3-ethyl-2-formyl-5,6,7,8-tetrahydro-5,5,8,8-tetramethylnaphthalene and 22.5 g (0.2 mole) of potassium tert.-butylate were reacted for 1 hour to give 8.3 g (25%) of the title compound of melting point 72°–73° C., the reaction mixture being poured onto water and acidified, and the precipitate which had separated out being recrystallized from methanol and once again from isopropanol.

EXAMPLE 17

4-[(5,6,7,8-Tetrahydro-5,5,8,8-tetramethylnaphth-2-yl)-ethynyl]-benzamide

A mixture of 2.5 g (8 millimoles) of 4-[(5,6,7,8-tetrahydro-5,5,8,8-tetramethylnaphth-2-yl)-ethynyl]-benzonitrile (Example 1), 60 ml of tert.-butanol and 7.5 g of potassium hydroxide powder was refluxed for 4 hours. The mixture was cooled, poured onto saturated sodium chloride solution and extracted twice with ether. The ether phases were washed with sodium chloride solution, dried over $Na_2SO_4$ and evaporated down to give 2.2 g (83%) of the pure title compound of melting point 220°–223° C.

EXAMPLE 18

4-[(5,6,7,8-Tetrahydro-5,5,8,8-tetramethylnaphth-2-yl)-ethynyl]-benzaldehyde 56 ml (67 millimoles) of a 20% strength solution of diisobutylaluminum hydride in hexane were added to a solution of 10 g (32 millimoles) of 4-[(5,6,7,8-tetrahydro-5,5,8,8-tetramethylnaphth-2-yl)-ethynyl]-benzonitrile (Example 1) in 120 ml of absolute ether. The mixture was stirred for a further 40 minutes, 150 ml of saturated tartaric acid solution were added dropwise and stirring was continued for a further hour. Thereafter, the mixture was extracted three times with ether and the combined ether phases were washed twice with water, dried over $Na_2SO_4$ and evaporated down. Recrystallization of the residue from isopropanol gave 3.8 g (38%) of the title compound of melting point 130° C.

EXAMPLE 19

4-[(2,3-Dihydro-1,1,2,3,3-pentamethyl-5(1H)-indenyl)-ethynyl]-benzaldehyde

Using a procedure similar to that described in Example 1c, 8 g (40 millimoles) of (2,3-dihydro-1,1,2,3,3-pentamethyl-5(1H)-indenyl)-ethyne and 4.6 g (25 millimoles) of 4-bromobenzaldehyde were reacted, the solution was filtered and the filtrate was evaporated down to give a residue, which was extracted with sodium bicarbonate solution-methylene chloride. Stirring the residue with methylene chloride and a little cyclohexane gave 2.3 g (29%) of the title compound of melting point 106°-107° C.

EXAMPLE 20

4-[(5,6,7,8-Tetrahydro-5,5,8,8-tetramethylnaphth-2-yl)-ethynyl]-benzyl alcohol

A suspension of 15.8 g (48 millimoles) of 4-[(5,6,7,8-tetrahydro-5,5,8,8-tetramethylnaphth-2-yl)-ethynyl]-benzoic acid (Example 6) in 160 ml of absolute ether was added dropwise to a suspension of 1.9 g (49 millimoles) of lithium aluminum hydride in 150 ml of absolute ether. Thereafter, the mixture was stirred under reflux for 3 hours, after which 50 ml of ethyl acetate, 200 ml of water and 150 ml of 2N HCl were added dropwise in succession, and the phases were separated. The aqueous phase was extracted once again with ether, and the combined ether extracts were washed with water, dried over Na₂SO₄ and evaporated down. The oil which remained (17 g) was stirred with heptane, and the resulting crystals were filtered off under suction and dried. 7.2 g (48%) of the title compound of melting point 115°-117° C. were obtained in this manner.

EXAMPLE 21

4-[(5,6,7,8-Tetrahydro-5,5,8,8-tetramethylnaphth-2-yl)-ethynyl]-benzyl methyl ether A solution of 2 g (6.3 millimoles) of the benzyl alcohol derivative described in Example 20 above, in 10 ml of absolute dimethylformamide, was added dropwise to a suspension of 0.4 g (13 millimoles) of sodium hydride in 15 ml of absolute dimethylformamide at room temperature. Stirring was continued for 1 hour, after which 1.5 g (10 millimoles) of iodomethane were added dropwise. The mixture was heated at 60° C. for 15 hours, cooled and then poured onto water, and the precipitated solid was filtered off under suction. Recrystallization from methanol gave 0.8 g (38%) of the title compound of melting point 93°-94° C.

EXAMPLE 22

4-[(5,6,7,8-Tetrahydro-5,5,8,8-tetramethylnaphth-2-yl)-ethynyl]-benzyl acetate 1.7 ml of acetic anhydride were added to a mixture of 1.5 g (4.7 millimoles) of 4-[(5,6,7,8-tetrahydro-5,5,8,8-tetramethylnaphth-2-yl)-ethynyl]-benzyl alcohol (Example 20) and 8.7 ml of pyridine. The mixture was stirred for 16 hours at room temperature, after which it was poured onto ice/water and acidified. The precipitated solid was filtered off under suction, washed with water and dried. 1.3 g (77%) of the title compound of melting point 136°-139° C. were obtained in this manner.

EXAMPLE 23

4-[(5,6,7,8-Tetrahydro-5,5,8,8-tetramethylnaphth-2-yl)-ethynyl]-benzylamine

A solution of 8.2 g (26 millimoles) of 4-[(5,6,7,8-tetrahydro-5,5,8,8-tetramethylnaphth-2-yl)-ethynyl]-benzonitrile (Example 1) in 150 ml of absolute ether was added dropwise to a suspension of 2.8 g (73 millimoles) of lithium aluminum hydride in 150 ml of absolute ether at room temperature in the course of 25 minutes. The mixture was stirred under reflux for 3.5 hours and then cooled, after which water was added carefully, sodium sulfate solution was added dropwise and the phases were separated. The aqueous phase was extracted twice with ether, and the combined ether phases were washed once with water, dried over Na₂SO₄ and evaporated down. 7.7 g (93%) of the title compound of melting point 84°-88° C. remained.

EXAMPLE 24

N-Acetyl-4-[(5,6,7,8-tetrahydro-5,5,8,8-tetramethylnaphth-2-yl)-ethynyl]-benzylamine 2.5 g (25 millimoles) of acetic anhydride were added dropwise, at 0° C., to a mixture of 3.2 g (10 millimoles) of the benzylamine derivative described in Example 23 above and 20 ml of pyridine. Stirring was continued for 3 hours, and the mixture was left to stand overnight at room temperature. It was poured onto ice/water and acidified with 0.5N HCl, and the precipitated solid was filtered off under suction and dried to give 3.1 g (86%) of the title compound of melting point 220°-223° C.

EXAMPLE 25

(E)-4-[(5,6,7,8-Tetrahydro-5,5,8,8-tetramethylnaphth-2-yl)-ethynyl]-cinnamic acid Using a procedure similar to that described in Example 6b, 16.5 g (44 millimoles) of diethyl 1-chloro-1-(5,6,7,8-tetrahydro-5,5,8,8-tetramethylnaphth-2-yl)-methylphosphonate (about 85% strength), 7.8 g (44 millimoles) of 4-formylcinnamic acid and 15.5 g (137 millimoles) of potassium tert.-butylate were converted to 6.2 g (39%) of the title compound of melting point 256°-258° C. (from ethanol).

EXAMPLE 26

Ethyl (E)-4-[(5,6,7,8-tetrahydro-5,5,8,8-tetramethylnaphth-2-yl)-ethynyl]-cinnamate Using a procedure similar to that described in Example 11, 2 g (5.6 millimoles) of the cinnamic acid described in Example 25 above, 2.6 g of potassium carbonate and 1.8 g of iodoethane were converted to 2 g (93%) of the title compound of melting point 116°-118° C., the reaction mixture being poured onto water, and the precipitated solid filtered off under suction, washed with a little methanol and dried.

We claim:

1. A diarylacetylene of the formula I

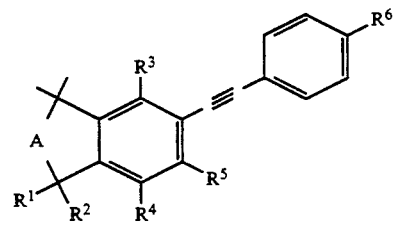

where $R^1$ and $R^2$ are each hydrogen or methyl, $R^3$ is hydrogen, methyl, hydroxy or $C_1$–$C_6$-alkoxy, $R^4$ is hydrogen, methyl or methoxy, $R^5$ is hydrogen, halogen, methoxy or $C_1$–$C_4$-alkyl, A is methylene or ethylene radical which is unsubstituted or substituted by $C_1$–$C_4$-alkyl or is —CH=CH—, —CHOH—CH₂— or —CO—CH₂— and $R^6$ is methyl, nitrile, CH₂—OR⁸, —CH$_2$—NHR$^9$, —COR$^{11}$ or —CH=CH—COOH, where R$^8$ is hydrogen, C$_1$-C$_4$-alkyl or C$_1$-C$_4$-alkanoyl, R$^9$ is hydrogen or C$_{1-6}$-alkanoyl and R$^{11}$ is hydrogen or NH$_2$, and its physiologically tolerated salts.

2. The compound of claim 1 which is 4-[(5,6,7,8-tetrahydro-5,5,8,8-tetramethylnaphth-2-yl)-ethynyl]-benzonitrile.

3. The compound of claim 1 which is 4-[(5,6,7,8-tetrahydro-5,5,8,8-tetramethylnaphth-2-yl)-ethynyl]-benzaldehyde.

4. The compound of claim 1 which is 4-[(5,6,7,8-tetrahydro-5,5,8,8-tetramethylnaphth-2-yl)-ethynyl]-benzyl alcohol.

5. A therapeutic composition comprising a pharmaceutically acceptable carrier and an effective amount of a compound according to claim 1 as the active compound.

6. The method of treating dermatological disorders in a patient suffering therefrom which comprises administering an effective amount of a compound according to claim 1.

* * * * *